United States Patent
Turner et al.

[11] Patent Number: 5,864,383
[45] Date of Patent: Jan. 26, 1999

[54] SINGLE-CURVATURE PLACIDO PLATE

[75] Inventors: Timothy N. Turner, West Valley City; Gregg D. Niven, Salt Lake City; Joseph R. Bentley, West Jordan; Edwin J. Sarver, Merritt Island; Charles R. Broadus, Ogden, all of Utah

[73] Assignee: Orbtek, Inc., Salt Lake City, Utah

[21] Appl. No.: 841,140

[22] Filed: Apr. 24, 1997

[51] Int. Cl.$^6$ ............................................. A61B 3/10
[52] U.S. Cl. ................................ 351/212; 351/47
[58] Field of Search ........................ 351/212, 247, 351/205

[56] References Cited

U.S. PATENT DOCUMENTS

| | | | |
|---|---|---|---|
| Re. 27,475 | 9/1972 | Volk | 351/212 |
| D. 345,213 | 3/1994 | Shalon et al. | D24/172 |
| 1,006,825 | 10/1911 | Buchhop | 351/212 |
| 1,750,931 | 3/1930 | Kellner et al. | 351/212 |
| 2,174,308 | 9/1939 | Hartinger | 351/212 |
| 2,250,521 | 7/1941 | Boeder | 351/212 |
| 3,248,162 | 4/1966 | Knoll | 351/212 |
| 3,290,927 | 12/1966 | Gambs | 351/212 |
| 3,486,812 | 12/1969 | Volk | 351/212 |
| 3,536,384 | 10/1970 | Cocks | 351/212 |
| 3,598,478 | 8/1971 | Townsley | 351/212 |
| 3,609,017 | 9/1971 | Nuchman | 351/212 |
| 3,634,003 | 1/1972 | Guyton | 351/205 |
| 3,797,921 | 3/1974 | Kilmer et al. | 351/212 |
| 3,895,860 | 7/1975 | Townsley | 351/212 |
| 3,932,030 | 1/1976 | Hasegawa et al. | 351/212 |
| 4,019,813 | 4/1977 | Cornsweet et al. | 351/212 |
| 4,157,859 | 6/1979 | Terry | 350/35 |
| 4,159,867 | 7/1979 | Achatz et al. | 351/212 |
| 4,172,639 | 10/1979 | Lang et al. | 351/212 |
| 4,256,385 | 3/1981 | Cohen et al. | 351/212 |
| 4,410,242 | 10/1983 | Muller et al. | 351/211 |
| 4,426,141 | 1/1984 | Holcomb | 351/212 |
| 4,456,348 | 6/1984 | Schulz et al. | 351/212 |
| 4,490,022 | 12/1984 | Reynolds | 351/211 |
| 4,491,398 | 1/1985 | Karickhoff | 351/211 |
| 4,540,254 | 9/1985 | Humphrey | 351/212 |
| 4,569,576 | 2/1986 | Karpov et al. | 351/212 |
| 4,597,648 | 7/1986 | Feldon et al. | 351/212 |
| 4,669,466 | 6/1987 | L'Esperance | 128/303.1 |
| 4,685,140 | 8/1987 | Mount, II | 382/6 |
| 4,772,115 | 9/1988 | Gersten et al. | 351/212 |
| 4,779,973 | 10/1988 | Miller et al. | 351/212 |
| 4,799,784 | 1/1989 | Safir | 351/212 |
| 4,817,432 | 4/1989 | Wallace et al. | 73/602 |

(List continued on next page.)

OTHER PUBLICATIONS

Koch et al., "Introduction To Corneal Topography", *Corneal Topography The State of the Art*, pp. 3–15, 1995.
Orbtek brochures, "Orbscan Total Anterior Chamber Eye Exam", 7 pages.

*Primary Examiner*—Huy Mai
*Attorney, Agent, or Firm*—Trask, Britt & Rossa

[57] ABSTRACT

An apparatus for analyzing a subject's cornea includes a frame having first and second ends, a single curvature (i.e. non-planar and non-axisymmetrical) screen associated with the first end of the frame, the non-planar and non-axisymmetrical screen having an opaque covering which is interrupted along its surface to form a pattern. A light source is disposed to cast the pattern placed on the screen onto the subject's cornea, thus causing a pattern to reflect therefrom. A light detector (e.g. a camera, CCD, or human eye) is disposed to sense the pattern reflected from the subject's cornea. The improved Placido plate is easier to manufacture. The design allows for incorporation of extremely complex pattern shapes, while its shape helps to maintain focus of the image.

15 Claims, 5 Drawing Sheets

U.S. PATENT DOCUMENTS

| | | | |
|---|---|---|---|
| 4,834,529 | 5/1989 | Barrett | 351/212 |
| 4,863,260 | 9/1989 | Gersten et al. | 351/212 |
| 4,995,716 | 2/1991 | Warnicki et al. | 351/212 |
| 4,998,819 | 3/1991 | Labinger et al. | 351/212 |
| 5,009,498 | 4/1991 | Gersten et al. | 351/212 |
| 5,018,850 | 5/1991 | Gersten et al. | 351/212 |
| 5,106,183 | 4/1992 | Yoder, Jr. | 351/212 |
| 5,159,361 | 10/1992 | Cambier et al | 351/212 |
| 5,194,882 | 3/1993 | Penney | 351/212 |
| 5,214,456 | 5/1993 | Gersten | 351/212 |
| 5,227,818 | 7/1993 | El Hage | 351/212 |
| 5,300,965 | 4/1994 | Kitajima | 351/212 |
| 5,347,331 | 9/1994 | Isogai et al. | 351/208 |
| 5,349,398 | 9/1994 | Koester | 351/212 |
| 5,357,294 | 10/1994 | Shimizu et al. | 351/212 |
| 5,384,608 | 1/1995 | Gersten | 351/212 |
| 5,406,342 | 4/1995 | Jongsma | 351/212 |
| 5,412,441 | 5/1995 | Tibbling et al. | 351/200 |
| 5,414,478 | 5/1995 | van Gelderen | 351/212 |
| 5,416,539 | 5/1995 | Gersten et al. | 351/212 |
| 5,418,582 | 5/1995 | van Saarloos | 351/212 |
| 5,418,714 | 5/1995 | Sarver | 364/413.13 |
| 5,475,452 | 12/1995 | Kuhn et al. | 351/212 |
| 5,512,965 | 4/1996 | Snook | 351/205 |
| 5,512,966 | 4/1996 | Snook | 351/205 |
| 5,526,072 | 6/1996 | El Hage | 351/208 |
| 5,585,873 | 12/1996 | Shalon et al. | 351/218 |

SINGLE-CURVATURE PLACIDO PLATE

TECHNICAL FIELD

The invention relates generally to corneal topographers for corneal screening, and more particularly to a single-curvature (i.e. non-planar and non-axisymmetrical) Placido plate.

BACKGROUND

The use of reflected Placido rings to analyze a subject's eye is known. For instance, in U.S. Pat. No. 3,248,162 (Apr. 26, 1966) to Knoll et al., various methods of positioning and illuminating a plurality of reflecting rings in front of a subject's cornea are identified. Such methods include photokeratoscopes wherein the rings are disposed on a plane surface which is held in front of the subject's cornea and illuminated by a light source and to one side of the cornea, reflecting rings formed on the interior surface of a sphere with the light source outside of the sphere, reflecting rings formed on the inner surface of a cylinder with the light source disposed outside of the cylinder, or reflecting rings disposed on the interior surface of a cylindrical cage with the light source disposed within the cage itself.

Illuminating the rings causes reflections of the rings to appear on the cornea, and these reflections are then depicted (e.g. either optically or by photography) and then analyzed by an eye specialist. The reflecting rings are circular, and deviations of the cornea from sphericity cause bumps or indentations indicative of irregularities in the cornea to be present in the reflections of the rings. Unequally spaced rings can be indicative of regular deviations from sphericity, and elliptical reflections may indicate a toric cornea.

Other devices which use reflecting patterns to analyze a subject's eye are described in U.S. Pat. No. 1,750,931 to Kellner et al. (Mar. 18, 1930), U.S. Pat. No. 5,018,850 to Gersten et al. (May 28, 1991), U.S. Pat. No. 4,772,115 to Gersten et al. (Sep. 20, 1988), U.S. Pat. No. 3,932,030 to Hasegawa et al. (Jan. 13, 1976), U.S. Pat. No. 5,194,882 to Penney (Mar. 16, 1993); U.S. Pat. No. 4,685,140 to Mount, II (Aug. 4, 1987); U.S. Pat. No. 5,227,818 to El Hage (Jul. 13, 1993); U.S. Pat. No. 5,416,539 to Gersten et al. (May 16, 1995); U.S. Pat. No. 5,418,582 to van Saarloos (May 23, 1995); and U.S. Pat. No. 5,526,072 to El Hage (Jun. 11, 1996).

Exemplary of these devices is U.S. Pat. No. 3,797,921 to Kilmer et al. (Mar. 19, 1974), the contents of which are incorporated by this reference. Kilmer et al. discloses a photographic apparatus for determining the corneal radius. The apparatus uses a transparent, concave screen having one or more opaque, concentric rings placed thereon. Light passes through the screen to the subject's eye, causing the concentric ring pattern to be reflected on the subject's eye. A photograph is taken and analyzed, and the corneal radius determined.

Although the aforementioned devices are usually adequate for most purposes, sometimes it is desirable to change the image or pattern illuminated by the apparatus (e.g. from a Placido ring pattern to a checkerboard pattern). Unfortunately, with the axisymmetrical shape of the Placido screens to date (e.g., on cylindrical and dish-shaped screens), changing the pattern has proven difficult. Planar screens, although potentially easier to change the pattern thereon, suffer from an inadequate reflective pattern for the amount of space used. It would thus be an improvement in the art to have an easy to manufacture non-planar screen which could be readily associated and disassociated with chosen patterns.

DISCLOSURE OF THE INVENTION

The invention includes an improvement in a Placido-type apparatus for analyzing the cornea of a subject, wherein the improvement comprises forming the screen to be non-planar and non-axisymmetrical, wherein the asymmetry is with respect to the apparatus' camera axis.

In general, an apparatus for analyzing a subject's cornea includes a frame having first and second ends. A single curvature (i.e. non-planar and non-axisymmetrical) screen is associated with the first end of the frame. The screen is associated with a partially opaque or translucent covering interrupted along its surface to form a illuminated pattern. A light source is disposed to cast the pattern placed on the screen onto the subject's cornea, thus causing a pattern to reflect therefrom. A light detector (e.g. a camera, CCD, or human eye) is disposed to sense the pattern reflected from the subject's cornea.

The improved Placido plate is easier to manufacture and experiment with, which may be useful in the diagnosis of a particular pathology. The design allows for incorporation of extremely complex patterns, while its shape helps to maintain focus of the image.

The invention also includes a method of making and using the Placido plate apparatus.

BRIEF DESCRIPTION OF THE DRAWINGS

In the drawings, which depict presently preferred embodiments of the invention and in which like reference numerals refer to like parts in different views.

BEST MODE OF THE INVENTION

Figure 1:
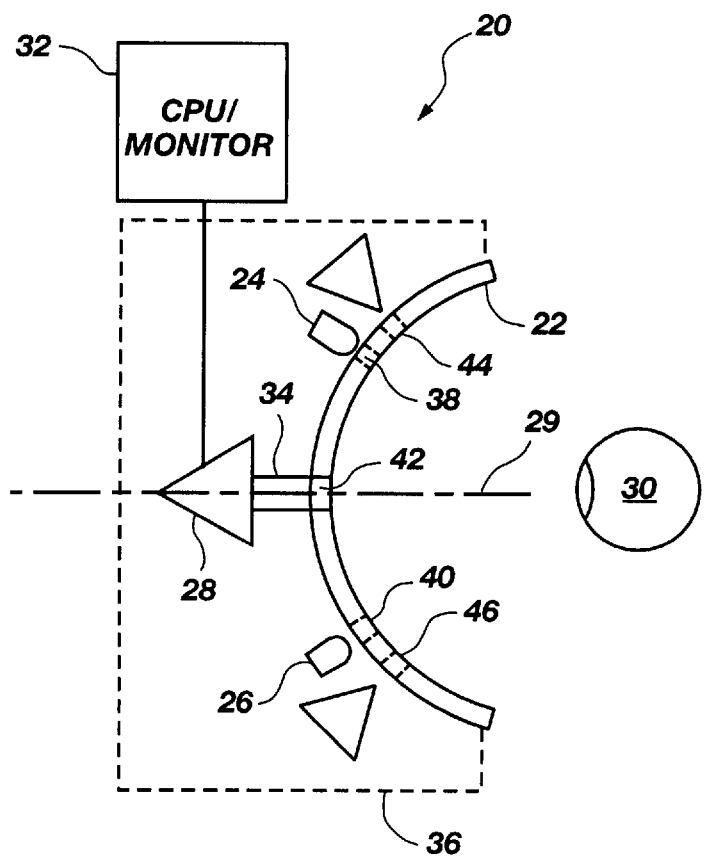
FIG. 1 is a stylized, top view of an apparatus according to the invention.

As depicted in FIG. 1, an apparatus, generally 20, for use with the single curvature screen preferably includes the screen 22, general facial illumination means 24, 26 (e.g. light emitting diodes or other incandescent or fluorescent lamps), a camera 28 or other means for recording, depicting, or viewing light reflected from the cornea of a subject's eye 30, and a computer 32 or other means for analyzing the light pattern reflected from the subject's eye. The preferred apparatus 20 is held together with a frame 34, table or similar means, and, when the light source is not associated with the construction of the screen, but is positioned behind a transparent screen for passing light therethrough (not shown), a housing 36 for containing the light and directing it towards the subject's face. Typically an adjustable chin rest or similar means will be incorporated into the device to keep the subject's face in the proper position.

Figure 2:
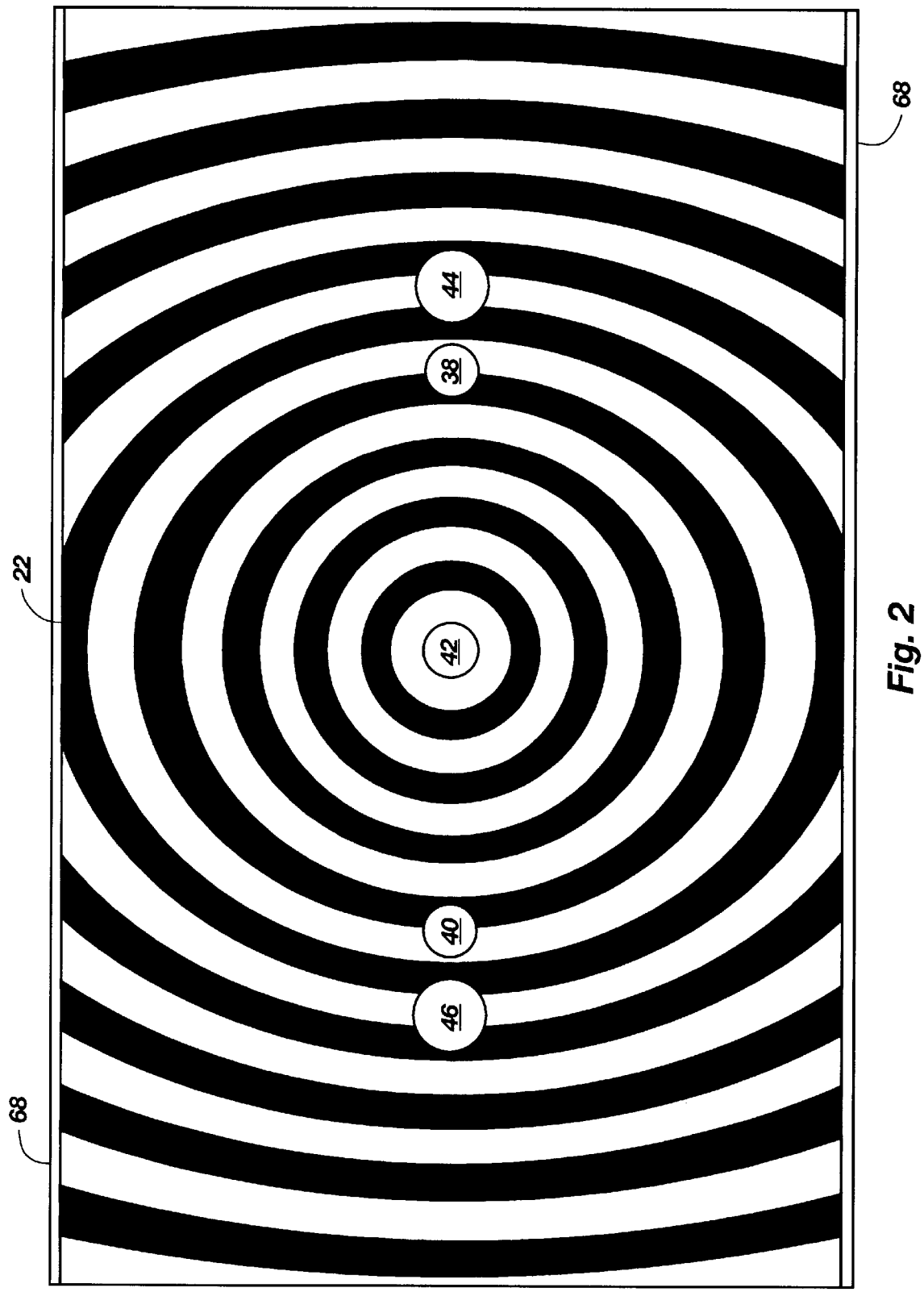
FIG. 2 is a flattened front view of a screen according to the invention depicting a Placido ring pattern.

As depicted in FIG. 2, the screen 22 has a plurality of apertures positioned therein. Two apertures 38, 40 are associated with the illumination means 24, 26 to allow illuminating light to pass from the illumination means through the screen 22 for illuminating the subject's face. One aperture 42 is positioned to allow the camera 28 or similar means to view the corneal pattern reflected from the subject's eye 30. The camera axis 29 runs from the camera 28 to the subject's eye 30. Other apertures 44, 46 may be provided to allow other types of analyses to be performed on the subject's eye such as a densitometer for ascertaining the thickness and relative optical density of a subject's cornea (see, e.g., U.S. Pat. Nos. 5,512,965 and 5,512,966 to Snook (Apr. 30, 1996)).

The depicted screen 22 is semi-cylindrical, being formed by, for example, rolling a rectangular member about a cylindrical member (or otherwise forming a generally circular cross-section), and extends from about 120° to about 180°, preferably from about 130° to about 150° about a 360° circumference. Shapes other than planar shapes may be used to form a non-planar, non-axisymmetric screen or plate. For instance, a square member or toric member may be used which results in a non-planar (after bending) and non-axisymmetrical (with respect to the camera axis) single-curvature screen.

Figure 3:
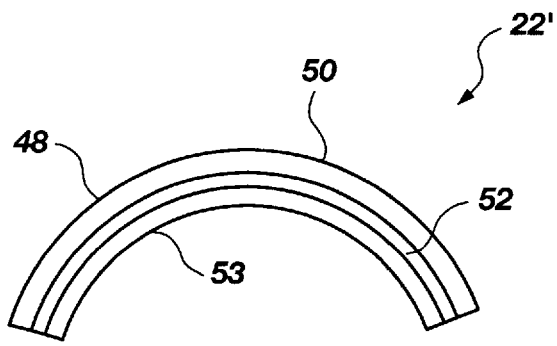
FIG. 3 is a top, cut-away view of a preferred embodiment of the invention.

A particularly preferred screen assembly 22' (with its components) is depicted in FIGS. 3–9. As depicted in FIG. 3, this screen 22' is a laminate comprising a back plate 48, an illuminator array 50, a light diffuser 52, and a front plate 53. The hereinafter described pattern is later associated with the front plate.

Figure 4:
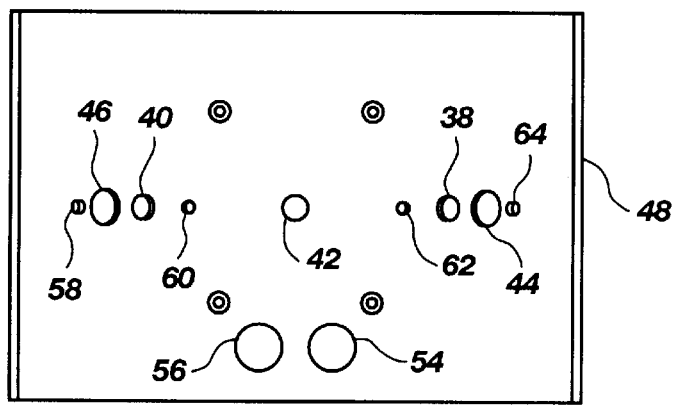
FIG. 4 is a front view of a back plate for incorporation in the screen assembly of the preceding figure.

FIG. 4 depicts the back plate 48. The back plate 48 is preferably made of a durable, opaque material, and may be plated. It has overall dimensions of from about twenty-five (25) to about thirty-five (35) centimeters (ten (10) to about fourteen (14) inches) in length, and from about ten (10) to about eighteen (18) (four (4) to about seven (7) inches) in height. It protects the diffuser and associated circuitry of the more thoroughly hereinafter described illuminator array 50. It has the previously described apertures 38–46 as well as apertures 54, 56 for allowing wiring to access the illuminator array 50 and apertures 58, 60, 62, 64 for assembling and constructing the screen. The assembly apertures 58–64 preferably have threaded inserts (not shown) associated therewith for receiving a screw, bolt or other threaded member for assembling the device.

Figure 5:
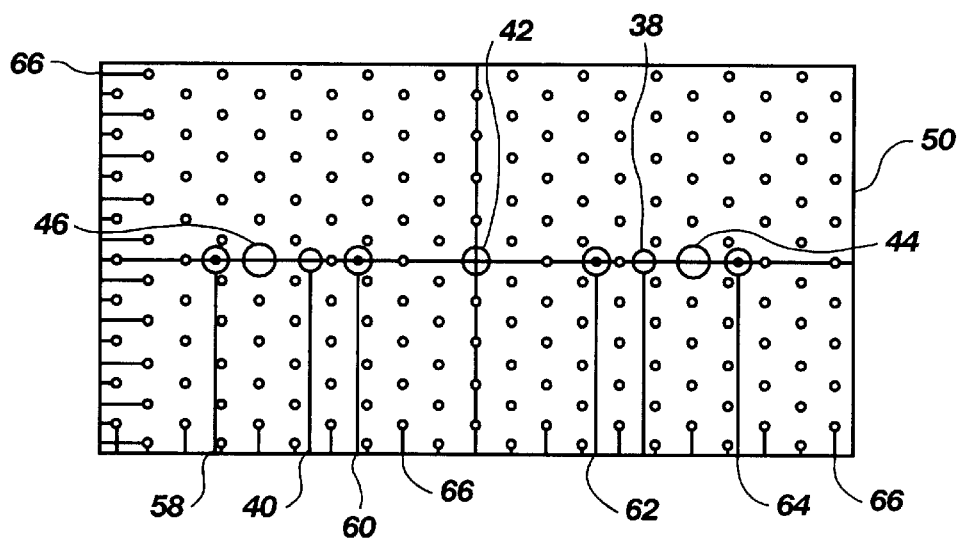
FIG. 5 is a flattened front view of an illuminator array for incorporation in the screen assembly of the preceding two figures.
Figure 6:
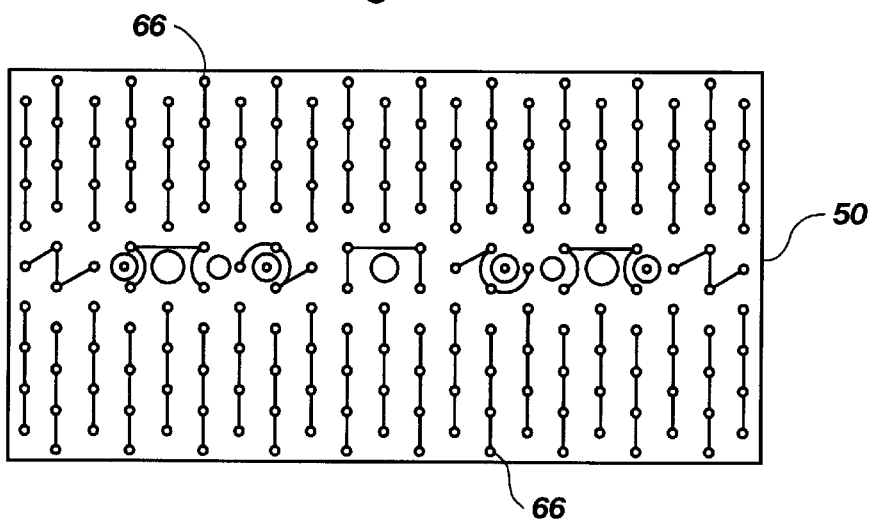
FIG. 6 is a back view of the illuminator array of the preceding figure showing electronic circuitry for illuminating the LED's.
Figure 7:
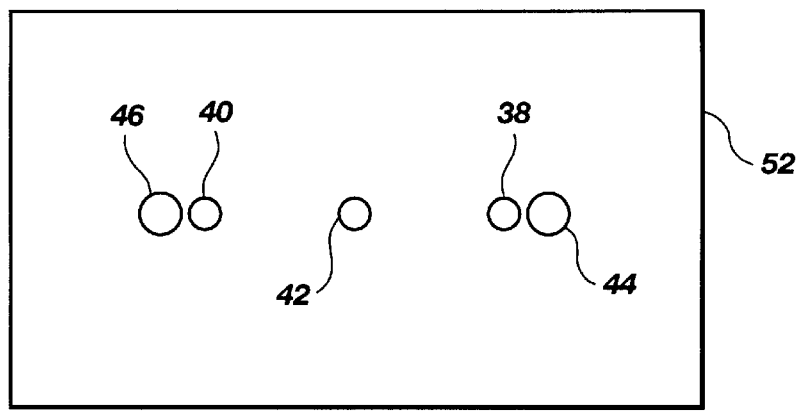
FIG. 7 is a flattened front view of a diffuser for incorporation in the screen assembly of the preceding five figures.
Figure 8:
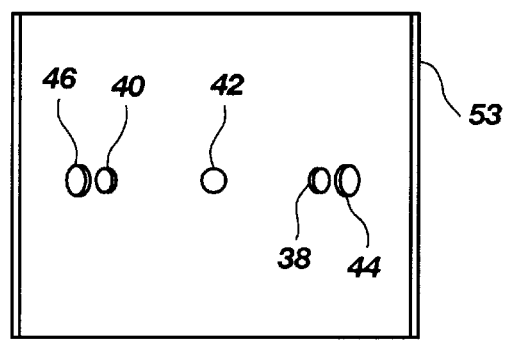
FIG. 8 is a front view of a front plate for use with the screen assembly of the preceding six figures.
Figure 9:
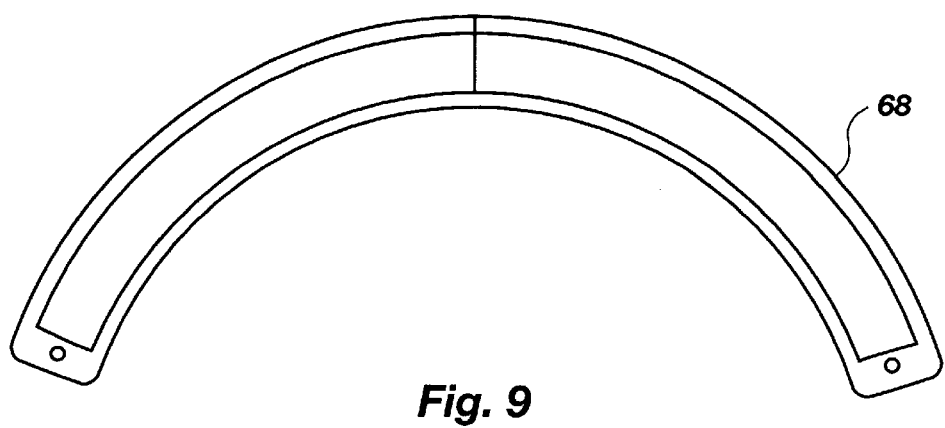
FIG. 9 is a top view of a cover plate for use with the screen assembly of the preceding seven figures.

FIGS. 5 and 6 more thoroughly depict the illuminator array 50 for use with the preferred screen. The illuminator array is of a size selected to be contained within the arced back plate 48. LEDs 66 are distributed about the illuminator array and provide a light source for illuminating a pattern on the screen 22 (e.g. projecting the pattern from the screen). Any suitable power source may be used to power the LEDs.

The diffuser 52 (FIG. 7) diffuses the light from the LEDs 66 associated with the illuminator array. It too is sized to be associated with the illuminator array 50 and back plate 48. It is preferably made of an about 10 mil thick velvet finish clear polycarbonate sheet.

The front plate 53 (FIG. 8) is preferably a translucent white acrylic sheet sized to cover the diffuser 52 sandwiched between the front plate 53 and the illuminator array 50.

A pair of cover plates (one cover plate 68 depicted in FIG. 9) are assembled as a floor and ceiling (or "end caps") containing the rest of the screen assembly 22, and is preferably used to contain the remainder of the screen assembly components in operable orientation with one another.

Onto the front plate 53 is adhered the pattern. Adherence may be by adhesive, interacting strips (e.g. VELCRO™), clips, or equivalent means. Other means for adhering the pattern include the use of a lip around the edge of the screen (e.g. by interaction of the cover plates with the remainder of the screen assembly).

Figure 10:
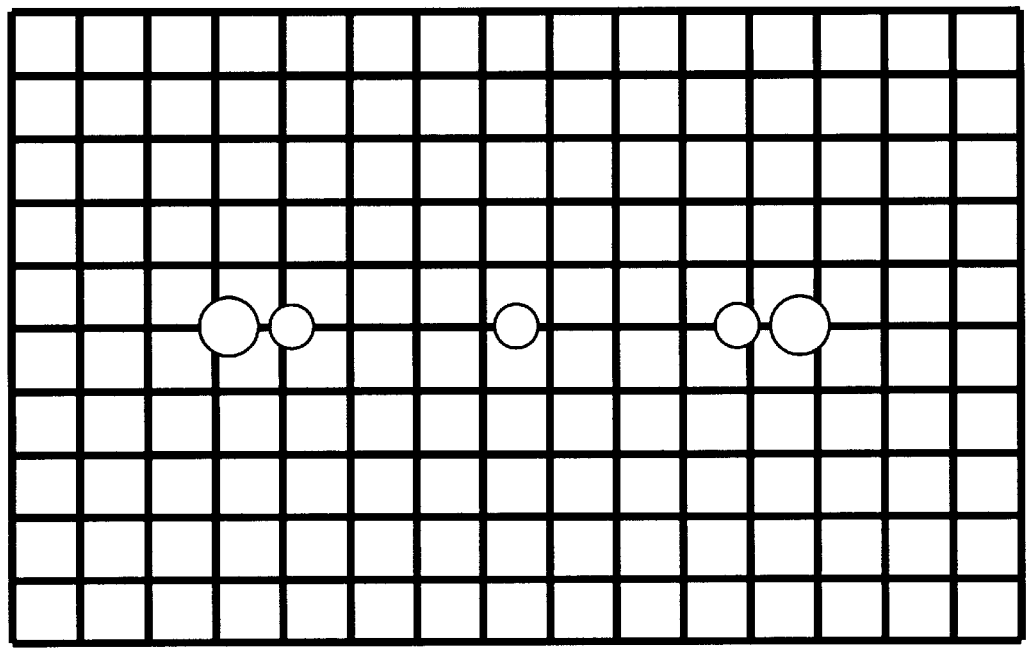
FIG. 10 is a flattened front view of a pattern to be illuminated on a screen assembly according to the invention.
Figure 11:
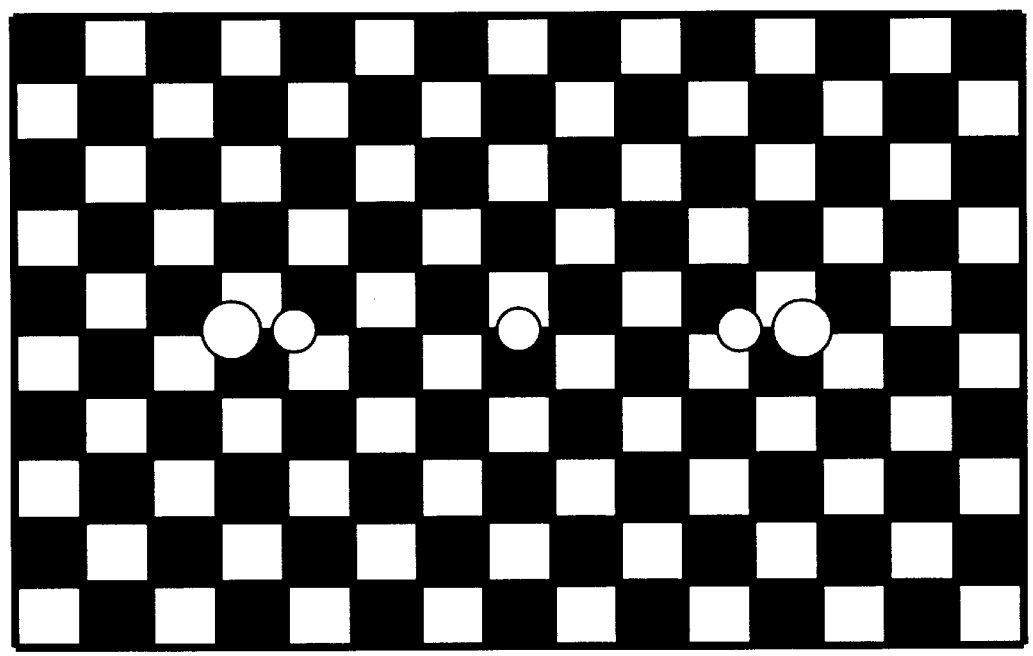
FIG. 11 is a flattened front view of another pattern to be illuminated on a screen assembly according to the invention.

A preferred pattern is that depicted in FIG. 2 (i.e. Placido rings). Alternatively however, patterns such as grid works (FIG. 10), checkerboards (FIG. 11), quadrants, ellipses, and mixtures thereof can be used (not shown).

The optically detectable pattern can be applied to the surface by various means. Patterns can be printed out on a laser printer or plotter onto a suitable polymer. In one highly preferred embodiment, an opaque pattern is printed onto a transparent polycarbonate sheet laminated to an appropriately sized adhesive tape (e.g. SCOTCH 467MP HI PERFORMANCE adhesive tape available from 3M Company of St. Paul, Minn.). The pattern may then be selected for the particular application, prepared, printed up and quickly applied to the screen. If a better pattern is discovered, it is much easier to upgrade the pattern since "decals" containing the pattern can be quickly made and easily adhered to the screen in existing diagnostic units.

In models where light passes through the screen from a light source (e.g. a 40 Watt bulb), the focussing screen can be made of any suitable material. For instance, the focussing screen can be made of a transparent base formed of a polymer of an acrylic acid or an ester thereof, for example polymeric methacrylate (e.g. LUCITE™).

The apparatus can be modified like similar devices. For instance, a computerized system for displaying an image of a keratograph taken by a video camera on a video monitor and determining the position and/or dimensions of Placido rings on the keratograph and then selectively correcting the measured data is disclosed in U.S. Pat. No. 4,685,140 to Mount, II (Aug. 4, 1987). In that device, an interface circuit is provided which digitizes and stores in the computer memory one video scan line at a time, and contains ring data storage and logic for superimposing ring data on the keratograph image. An apparatus and technique for automatically centering and focusing a corneal topographer is disclosed in U.S. Pat. No. 5,526,072 to El Hage (Jun. 11, 1996). Methods of using a charge coupled device are disclosed in U.S. Pat. No. 5,227,818 to El Hage (Jul. 13, 1993). These ideas and others may be incorporated into the instant device.

Once having been apprised of the improved Placido plate according to the instant invention, those of skill in the art will be readily able to make and use them.

Furthermore, although the invention has been described with a certain degree of particularity in structure, reference herein to details of the illustrated embodiments has been made by way of example only, and numerous changes in structural details may be resorted to without departing from the scope of the following claims. For instance, although the invention is preferably for use with a table-mounted unit (since hand-held models lose too much vertical) which use a camera or CCD, the invention can be applied to hand held models.

What is claimed is:

1. An apparatus for analyzing a subject's cornea, said apparatus comprising:

a frame having first and second ends;

a single curvature screen associated with the first end of the frame, the single curvature screen having an opaque covering which is interrupted along its surface to form an illuminated pattern;

a light source disposed to cast the illuminated pattern onto the subject's cornea thus causing the pattern to reflect therefrom; and a light detector for sensing the pattern reflected from the subject's cornea.

2. The apparatus of claim 1 further comprising:

a monitor for receiving signals from said light detector and for displaying images of the pattern reflected from the subject's cornea.

3. The apparatus of claim 1 wherein said single curvature screen is shaped in the form of a semi-cylinder.

4. The apparatus of claim 1 wherein the pattern is a series of generally concentric rings.

5. The apparatus of claim 1 wherein the pattern is a checkerboard pattern.

6. The apparatus of claim 1 wherein the pattern is a gridwork pattern.

7. The apparatus of claim 1 wherein the pattern is detachably associated with the single curvature screen.

8. The apparatus of claim 1 wherein the single curvature screen comprises a screen assembly including:

a back plate, a light diffuser having first and second sides, an illuminator array sandwiched between said back plate and the first side of said light diffuser, and a front plate associated with the second side of the light diffuser.

9. An improvement in an apparatus for analyzing a cornea of a subject, said apparatus of the type wherein an optically detectable pattern disposed on a screen is cast onto the subject's cornea from which the optically detectable pattern is reflected and reflections of the optically detectable pattern on the cornea are analyzed, the improvement comprising:

forming said screen to be a single curvature, but non-planar and non-axisymmetrical, screen.

10. The improvement of claim 9 wherein said single curvature screen is shaped in the form of a semi-cylinder.

11. The improvement of claim 9 wherein the optically detectable pattern is a series of generally concentric rings.

12. The improvement of claim 9 wherein the optically detectable pattern is a checkerboard pattern.

13. The improvement of claim 9 wherein the optically detectable pattern is a gridwork pattern.

14. The improvement of claim 9 wherein the optically detectable pattern is detachably associated with the screen.

15. The improvement of claim 10 wherein the semi-cylindrical screen comprises a screen assembly including:

a back plate, a light diffuser having first and second sides, an illuminator array sandwiched between said back plate and the first side of said light diffuser, and a front plate associated with the second side of the light diffuser.

* * * * *